United States Patent [19]

Rizzo et al.

[11] 3,947,591

[45] Mar. 30, 1976

[54] PESTICIDAL N,N''-THIO AND DITHIO BIS(SUBSTITUTED PHENYL FORMAMIDINES)

[75] Inventors: Victor L. Rizzo, Almena Township, Van Buren County; Alan R. Friedman, Kalamazoo, both of Mich.

[73] Assignee: The Upjohn Company, Kalamazoo, Mich.

[22] Filed: May 7, 1975

[21] Appl. No.: 575,248

[52] U.S. Cl. ........ 424/326; 260/501.14; 260/551 S; 260/564 RF
[51] Int. Cl.² ............... C07C 123/00; C07C 145/02
[58] Field of Search ................... 424/326; 260/551 S

[56] References Cited
UNITED STATES PATENTS

| | | | |
|---|---|---|---|
| 3,819,701 | 6/1974 | Takahashi et al. | 424/326 X |
| 3,887,619 | 6/1975 | Rizzo | 424/326 X |

FOREIGN PATENTS OR APPLICATIONS

| | | | |
|---|---|---|---|
| 831,075 | 3/1960 | United Kingdom | 424/326 |

OTHER PUBLICATIONS
Yamamoto et al., CA 79:122570n (1973).
Duerr et al., CA 76:59252f (1972).
Kurzer et al., CA 52:9089i (1958).

*Primary Examiner*—Robert V. Hines
*Assistant Examiner*—Thomas A. Waltz
*Attorney, Agent, or Firm*—John J. Killinger; Roman Saliwanchik

[57] ABSTRACT

Novel pesticidal compounds of the formula:

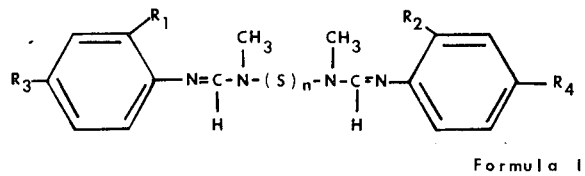

Formula I wherein $R_1$ and $R_2$ are the same or different and are selected from the group consisting of lower alkyl of from 1 to 4 carbon atoms; $R_3$ and $R_4$ are the same or different and are selected from the group consisting of hydrogen, halogen, and lower alkyl of from 1 to 4 carbon atoms, $n = 1$ or 2 provided that when $n$ is 2 then $R_1$ and $R_2$ are the same as $R_3$ and $R_4$ are the same.

The compounds are combined with carriers to prepare compositions and are useful in controlling insect pests either as an insecticide or behavioral modifier and are particularly effective as miticides.

25 Claims, No Drawings

PESTICIDAL N,N''-THIO AND DITHIO BIS(SUBSTITUTED PHENYL FORMAMIDINES)

CROSS REFERENCE TO RELATED APPLICATIONS

The starting materials for the compounds are disclosed in U.S. Application Ser. No. 366,999, filed June 1, 1973, now U.S. Pat. No. 3,887,619.

BRIEF SUMMARY OF THE INVENTION

Novel compounds of the Formula I, useful as insecticides, miticides, or insect behavioral modifiers. Compositions comprising a compound of the Formula I with a carrier and a method for reducing the population of undesirable insect pests.

DETAILED DESCRIPTION OF THE INVENTION

The compounds of the Formula I

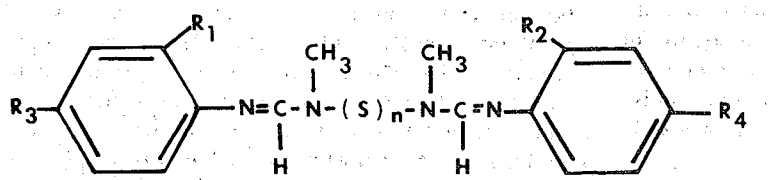

wherein $R_1$ and $R_2$ are the same, $R_3$ and $R_4$ are the same and $n$ is 1; are prepared by reacting 2 moles of a compound of the formula:

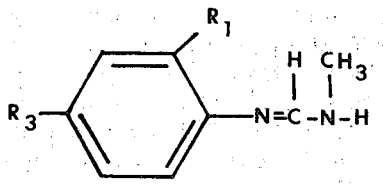

Formula II with 1 mole sulfur dichloride ($SCl_2$) in the presence of an acid scavenger.

Similarly, wherein $n$ is 2, sulfur monochloride (Cl-S-S-Cl) is substituted for sulfur dichloride.

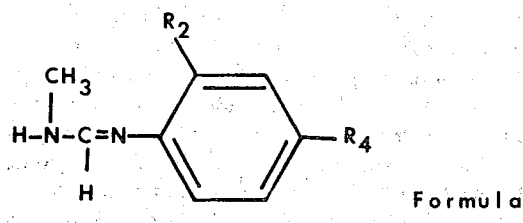

Formula III

To prepare compounds of the Formula I wherein $R_1$ and $R_2$ are different and $R_3$ and $R_4$ are different and $n$ is 1; one mole of compound of Formula II with substituents $R_1$ and $R_3$ is reacted with one mole of sulfur dichloride in the presence of one mole of tertiary amine and is then added to one mole of compound of Formula III with substituents $R_2$ and $R_4$ in the presence of one mole of tertiary amine.

The procedure is also applicable when $R_1$ and $R_2$ are the same (or different) and $R_3$ and $R_4$ are the same (or different).

In the foregoing formulae $R_1$ and $R_2$ are the same or different and are selected from the group consisting of lower alkyl of from 1 to 4 carbon atoms, $R_3$ and $R_4$ are the same or different and are selected from the group consisting of hydrogen, halogen, and lower alkyl of from 1 to 4 carbon atoms.

Lower alkyl of from 1 to 4 carbon atoms can be methyl, ethyl, propyl, butyl or isomeric forms thereof. Halogen can be fluorine, chlorine, bromine, or iodine.

The starting compounds of the Formula II are disclosed in copending application Ser. No. 366,999, filed June 1, 1973, now U.S. Pat. No. 3,887,619.

The above described reactions are advantageously carried out in the presence of an inert organic solvent. An inert organic solvent is defined herein as a solvent for the formamidine reactant (II) which does not enter into reaction with the reaction mixture components or in any way alter the desired course of the reaction. Illustrative of inert organic solvents are tetrahydrofuran, benzene, diethylether, and methylene chloride. Preferred as the inert organic solvent is tetrahydrofuran.

The proportion of solvent employed is not critical, but advantageously is a sufficient quantity to solubilize the reactant formamidine (II).

During the course of the above illustrated reaction, hydrochloric acid is generated as a by-product. Preferably this acid is removed from the reaction mixture as it forms. This may be accomplished by conventional and known methods, for example by adding an acid acceptor compound to the reaction mixture. Examples of acid acceptor compounds are the tertiary amines such as trimethylamine, triethylamine, tripropylamine, tributylamine, pyridine and the like.

Although the above reaction may be carried out over a broad range of temperature conditions, i.e., from about −30° C. to about reflux temperature for the reaction mixture, it is preferably carried out at about 0° C.

Progress of the above reaction may be followed by conventional analytical methods, such as for example by nuclear magnetic resonance analysis which will show spectral characteristics of the product compounds (I) or by thin-layer chromatography which will show the appearance of product compounds (I). Upon completion of the reaction, the desired compounds (I) are readily separated from the reaction mixture by conventional methods such as by filtration to remove solid residues and distillation to remove solvents.

The compounds of the Formula I are particularly advantageous commercially as invertebrate pesticides. For example, they are relatively stable both in storage and upon application in the field thus providing a long-lasting residual effectiveness.

In addition to killing invertebrate pests on contact, the compounds of the invention are absorbed by the vascular system of many plants, for example by cotton plants, and act systemically to kill the adult pests feeding upon the plant. Thus their period of pesticidal activity is further extended and non-feeding insects, i.e., insects not harmful to the plant are not unnecessarily killed during the whole period of pesticidal activity.

Compounds of the invention are also ovicidal, and are particularly effective in the control of acarine pest populations by this ovicidal action. Lepidopterous ova are also particularly susceptible to the compounds of the invention.

The compounds of the Formula I are also advantageous in that they exhibit relatively low mammalian toxicity and are non-phytotoxic at effective concentrations.

The invention also comprises invertebrate pesticidal compositions which comprise a pesticidally acceptable carrier and a pesticidally effective amount of a compound (I) of the invention. The compositions are useful in the method of the invention which is a process for controlling invertebrate pests, which comprises applying to a situs, effective amounts of the compounds (I) of the invention.

By the term "situs" I mean plants such as ornamentals, food crops, fruit trees, textile producing plants, berry bushes, lumber forests, farm yards, animal shelters, buildings, sanitary land-fill areas and like sites which are infected with or are potential infestation sites for invertebrate pests controllable with the compounds (I) of the invention.

The novel compounds (I) of the invention are useful in controlling invertebrate pest populations, i.e., in killing adults and ova of invertebrate pests or animals of the Phylum Arthropoda, for example those of Class Insecta such as those of the order Coleoptera as illustrated by the cotton boll weevil (*Anthonomus grandis* Boheman); those of the order Lepidoptera as illustrated by the southern army worm (*Prodenia eridania* Cramer); those of Class Arachnida such as those of the order Acarina as illustrated by the two-spotted spider mite (*Tetranychus telarius* Linnaeus or *Tetranychus urticae* Koch).

In addition to being effective in pest control through to modality of lethal effect, the compounds are effective in control as a behavioral modifier. For example young Lepidopteran larvae, aphids and mites are repelled by the chemicals on treated foliage, resulting in a marked reduction in population density. Adult moths are repelled and refuse to oviposity on treated plant parts. In addition, adult moths undergo chronic toxicity symptoms, i.e., increased wing beating with a resultant loss of wing scales and a premature death.

The following examples are illustrative of the process and products of the present invention but are not to be construed as limiting.

EXAMPLE 1

N,N''-Dithiobis[N'-(2-methyl-4-chlorophenyl)-N-methylformamidine]

To 3.65 g. (0.02 mole) of N-methyl-N'-(2-methyl-4-chlorophenyl)formamidine in 100 ml. tetrahydrofuran is added 2.22 g. (0.022 mole) triethylamine. The reaction mixture is cooled to 10° C. in an ice bath and 1.35 g. (0.02 mole) sulfur monochloride is added to the stirred solution. The reaction mixture is stirred without cooling for ½ hour. The solid is filtered off and the solvent removed. The residue is chromatographed over 100 g. of silica gel using benzene as the solvent to obtain 2.0 g. (47% yield) of a white crystalline product which has a melting point of 56°–57° C.

Analysis: Calc'd. for $C_{18}H_{20}Cl_2N_4S_2$: C, 50.58; H, 4.72; N, 13.11. Found: C, 50.44; H, 4.98; N, 13.00.

EXAMPLE 2

N,N''-Thiobis[N'-(2-methyl-4-chlorophenyl)-N-methylformamidine]

To 23.74 g. (0.13 mole) N-methyl-N'-(2-methyl-4-chlorophenyl)formamidine in 250 ml. tetrahydrofuran is added 14.14 g. (0.14 mole) triethylamine. The reaction mixture is cooled to 10° C. in an ice bath and 6.7 g. (0.065 mole) of sulfur dichloride is added to the stirred solution. The reaction mixture is stirred without cooling for ½ hour, the solid filtered off, the solvent removed, and the product recrystallized from Skellysolve B to obtain a white crystalline product, 16.3 g. (65% yield), m.p. 124°–126° C.

Analysis: Calc'd. for $C_{18}H_{20}Cl_2N_4S$: C, 54.68; H, 5.10; N, 14.17. Found: C, 54.89; H, 5.14; N, 14.00.

EXAMPLE 3

N'-(2-methyl-4-chlorophenyl)-N'''-2,4-xylyl-N,N''-thiobis[N-methylformamidine]

To a solution of 9.13 g. (0.05 mole) of N-methyl-N'-(2-methyl-4-chlorophenyl)formamidine in 200 ml. of methylene chloride is added 5.05 g. (0.05 mole) of triethylamine. The reaction mixture is cooled to –10° C. and a solution of 5.15 g. (0.05 mole) sulfur dichloride in 5 ml. methylene dichloride is added dropwise keeping the temperature below 0° c. After addition the reaction mixture is allowed to warm to 15° C. About two-thirds of the methylene chloride is removed and 200 ml. of hexane added. The remainder of the methylene chloride is removed and an additional 100 ml. of hexane added. This suspension containing the formamidine sulfenyl chloride is added quickly to a solution of 8.1 g. (0.05 mole) N-methyl-N'-2,4-xylylformamidine and 5.05 g. triethylamine in 300 ml. of hexane with cooling and stirring. The reaction mixture is stirred for 1 hour at room temperature, filtered, and the solvent removed to leave a solid. The crude product is taken up in 200 ml. hexane solution and extracted with 6 g. of citric acid in 100 ml. of water. The hexane solution is dried over $MgSO_4$, filtered, the solvent removed, and the residue recrystallized from Skellysolve B to yield 3.5 g. (18.6%) of product, m.p. 96°–98° C.

Analysis: Calc'd. for $C_{19}H_{23}ClN_4S$: C, 60.87; H, 6.18; N, 14.94. Found: C, 60.82; H, 5.96; N, 14.84.

EXAMPLE 4

N,N''-Thiobis[N'-2,4-xylyl-N-methylformamidine]

Following the procedure of Example 2 but substituting N-methyl-N'-2,4-xylylformamidine for N-methyl-N'-(2-methyl-4-chlorophenyl)formamidine, and toluene for tetrahydrofuran, the product is collected as a light amber oil (85% yield). The TLC and NMR were reasonable for the desired product.

Analysis: Calc'd. for $C_{20}H_{26}N_4S$: C, 67.76; H, 7.39; N, 15.80; S, 9.05. Found: C, 67.48; H, 7.62; N, 15.61; S, 9.27.

EXAMPLE 5

N,N''-Thiobis[N'-(2-methyl-4-bromophenyl)-N-methylformamidine]

Following the procedure of Example 2 but substituting N-methyl-N'-(2-methyl-4-bromophenyl)formamidine for N-methyl-N'-(2-methyl-4-chlorophenyl)formamidine the product is collected and recrystallized from ethyl acetate to obtain a white crystalline product (57% yield), m.p. 127°–129° C.

Analysis: Calc'd. for $C_{18}H_{20}Br_2N_4S$: C, 44.65; H, 4.16; N, 11.57. Found: C, 44.42; H, 4.34; N, 11.34.

EXAMPLE 6

N,N''-Dithiobis[N'-2,4-xylyl-N-methylformamidine]

Following the procedure of Example 1, but substituting N-methyl-N'-2,4-xylylformamidine for N-methyl-N'-(2-methyl-4-chlorophenyl)formamidine the product is chromatographed over silica gel to obtain a viscous oil. The NMR and TLC were reasonable for the desired product.

Analysis: Calc'd. for $C_{20}H_{26}N_4S_2$: C, 62.12; H, 6.78; N, 14.49. Found: C, 61.69; H, 6.88; N, 14.15.

EXAMPLE 7

N,N''-Dithiobis[N'-(2-methyl-4-bromophenyl)-N-methylformamidine]

Following the procedure of Example 1, but substituting N-methyl-N'-(2-methyl-4-bromophenyl)formamidine for N-methyl-N'-(2-methyl-4-chlorophenyl)formamidine the product is recrystallized from ethyl acetate to obtain a white crystalline product (67% yield), m.p. 102°–104° C. The NMR was reasonable for the desired product.

Analysis: Calc'd. for $C_{18}H_{20}Br_2N_4S_2$: C, 41.87; H, 3.90; N, 10.85. Found: C, 42.15; H, 3.93; N, 10.95.

EXAMPLE 8

N,N''-Thiobis[N'-(2-methyl-4-iodophenyl)-N-methylformamidine]

Following the procedure of Example 2 but substituting N-methyl-N'-(2-methyl-4-iodophenyl)formamidine for N-methyl-N'-(2-methyl-4-chlorophenyl)formamidine the product is prepared.

EXAMPLE 9

N,N''-Thiobis[N'-o-tolyl-N-methylformamidine]

Following the procedure of Example 2, but substituting N-methyl-N'-o-tolylformamidine for N-methyl-N'-(2-methyl-4-chlorophenyl)formamidine the product is prepared.

EXAMPLE 10

N,N''-Thiobis[N'-(2,4-diethylphenyl)-4-methylformamidine]

Following the procedure of Example 2, but substituting N-methyl-N'-2,4-diethylphenylformamidine for N-methyl-N'-(2-methyl-4-chlorophenyl)formamidine the product is prepared.

EXAMPLE 11

N,N''-Thiobis[N'-(2-ethyl-4-chlorophenyl)-N-methylformamidine]

Following the procedure of Example 2, but substituting N-methyl-N'-(2-ethyl-4-chlorophenyl)formamidine for N-methyl-N'-(2-methyl-4-chlorophenyl)formamidine the product is prepared.

EXAMPLE 12

N,N''-Thiobis[N'-(2-isopropyl-4-chlorophenyl)-N-methylformamidine]

Following the procedure of Example 2, but substituting N-methyl-N'-(2-isopropyl-4-chlorophenyl)formamidine for M-methyl-N'-(2-methyl-4-chlorophenyl)formamidine the product is prepared.

EXAMPLE 13

N,N''-Thiobis[N'-(2-methyl-4-fluorophenyl)-N-methylformamidine]

Following the procedure of Example 2, but substituting N-methyl-N'-(2-methyl-4-fluorophenyl)formamidine for N-methyl-N'-(2-methyl-4-chlorophenyl)formamidine the product is prepared.

EXAMPLE 14

N,N''-Dithiobis[N'-(2-methyl-4-iodophenyl)-N-methylformamidine]

Following the procedure of Example 1 but substituting N-methyl-N'-(2-methyl-4-iodophenyl)formamidine for N-methyl-N'-(2-methyl-4-chlorophenyl)formamidine the product is prepared.

EXAMPLE 15

N,N''-Dithiobis[N'-(o-tolyl-N-methylformamidine]

Following the procedure of Example 1, but substituting N-methyl-N'-o-tolylformamidine for N-methyl-N'-(2-methyl-4-chlorophenyl) formamidine, the product is prepared.

EXAMPLE 16

N,N''-Dithiobis[N'-(2-ethyl-4-chlorophenyl)-N-methylformamidine]

Following the procedure of Example 1, but substituting N-methyl-N'-(2-ethyl-4-chlorophenyl)formamidine for N-methyl-N'-(2-methyl-4-chlorophenyl) formamidine, the product is prepared.

EXAMPLE 17

N,N''-Dithiobis[N'-(2,4-diethylphenyl)-N-methylformamidine]

Following the procedure of Example 1, but substituting N-methyl-N'-2,4-diethylphenylformamidine for N-methyl-N'-(2-methyl-4-chlorophenyl)formamidine, the product is prepared.

EXAMPLE 18

N,N''-Dithiobis[N'-(2-isopropyl-4-chlorophenyl)-N-methylformamidine]

Following the procedure of Example 1, but substituting N-methyl-N'-(2-isopropyl-4-chlorophenyl)formamidine for N-methyl-N'-(2-methyl-4-chlorophenyl)formamidine, the product is prepared.

EXAMPLE 19

N,N''-Dithiobis[N'-(2-methyl-4-fluorophenyl-N-methylformamidine]

Following the procedure of Example 1, but substituting N-methyl-N'-(2-methyl-4-fluorophenyl)formamidine for N-methyl-N'-(2-methyl-4-chlorophenyl)formamidine, the product is prepared.

EXAMPLE 20

N'-(2-methyl-4-chlorophenyl)-N'''-(2,4-diethylphenyl)-N,N''-thiobis[N-methylformamidine]

Following the procedure of Example 3, but substituting N-methyl-N'-2,4-diethylphenylformamidine for N-methyl-N'-2,4-xylylformamidine, the product is prepared.

EXAMPLE 21

N'-(2-ethyl-4-chlorophenyl)-N'''-(2-ethyl-4-bromophenyl)-N,N''-thiobis[N-methylformamidine]

Following the procedure of Example 3, but substituting N-methyl-N'-(2-ethyl-4-chlorophenyl)formamidine for N-methyl-N'-(2-methyl-4-chlorophenyl)formamidine, and N-methyl-N'-(2-ethyl-4-bromophenyl)formamidine for N-methyl-N'-2,4-xylylformamidine, the product is prepared.

EXAMPLE 22

N'-(2-isopropyl-4-fluorophenyl)-N'''-2,4-xylyl-N,N''-thiobis[N-methylformamidine]

Following the procedure for Example 3, but substituting N-methyl-N'-(2-isopropyl-4-fluorophenyl)formamidine for N-methyl-N'-(2-methyl-4-chlorophenyl)formamidine, the product is prepared.

The pesticidal compounds (I) may be employed to control invertebrate pest populations, in their pure forms. However, it is preferred that they be applied to a situs in the form of a composition, comprising the compound (I) and a pesticidally acceptable diluent or carrier. Pesticidally acceptable carriers or diluents are well known in the art. For example, those compounds (I) which are solids at ambient temperatures may be formulated as granulars, dusts, wettable powders, emulsifiable concentrates, aqueous dispersions, solutions, and flowable creams for application to insects, mites, objects, or a situs. Those compounds (I) which are liquids at ambient temperatures may be formulated as emulsifiable concentrates, aqueous dispersions, suspensions, solutions, aerosols and the like.

Illustratively, dusts are readily formulated by grinding a mixture of the solid compounds (I) and a pulverulent carrier in the presence of each other. Griding is conveniently accomplished in a ball mill, a hammer mill, or by air-blast micronization. A preferred ultimate particle size is less than 60 microns. Preferably, 95% of the particles are less than 50 microns, and about 75% are 5 to 20 microns. Dusts of that degree of comminution are conveniently free flowing and can be applied to inanimate matter, fruit trees, crop plants, and soil so as to effect thorough distribution and coverage. Dusts are particularly adapted for effectively controlling invertebrate pests such as insects and mites over wide areas when applied by airplane. They are also indicated for application to the undersides of plant foliage.

Representative pulverulent diluent carriers which are pesticidally acceptable are the natural clays such as China, Georgia, Barden, attapulgus, kaolin, and bentonite clays; minerals in their natural forms as they are obtained from the earth such as talc, pyrophyllite, quartz, diatomaceous earth, fuller's earth, chalk, rock phosphates and sulfates, sulfur, silica and silicates; chemically modified minerals such as washed bentonite, precipitated calcium silicate, synthetic magnesium silicate, and colloidal silica; and organic flours such as wood, walnut shell, soybean, cottonseed, and tobacco flours, and free-flowing hydrophobic starches.

Dusts may also be prepared by dissolving a compound (I) in a volatile solvent such as methylene chloride, mixing the solution with a pulverulent diluent carrier and evaporating the solvent.

The proportions of pulverulent carrier and compound (I) may be varied over a wide range depending upon the pests to be controlled and the conditions of treatment. In general, dust formulations contain up to about 50% (on a weight basis) of the compound (I) or a salt thereof as the active pesticide ingredient. Dusts having as little as 0.001% of the active ingredient may be used, but a generally preferred proportion is from about 0.50% to about 20% of the compound (I).

Dispersible powder formulations are prepared by incorporating a surfactant in a dust composition prepared as described above. By incorporating from 0.1% to about 12% of a surfactant in a dust, a dispersible powder is obtained which is particularly adapted for further admixture with water for spraying on inanimate matter and products, fruit trees, field crops, and soil. Such dispersible powders may be admixed with water to obtain any desired concentration of compound (I) and the mixture may be applied in amounts sufficient to obtain predetermined rates of application and uniform distribution. Preferably dispersible powders contain from about 10 percent to about 80 percent by weight of compound (I) as the active pesticide ingredient.

The surfactants employed may be characterized as capable of reducing the surface tension of water to less thatn about 40 dynes per centimeter in concentrations of about 1% or less.

Representative surfactants conventionally employed for preparing dispersible powder formulations include alkyl sulfates and sulfonates, alkyl aryl sulfonates, sulfosuccinate esters, polyoxyethylene sulfate, polyoxyethylenesorbitan monolaurate, alkyl-aryl polyester sulfates, alkylaryl polyether alcohols, alkyl naphthalene sulfonates, alkyl quaternary ammonium salts, sulfated fatty acids and esters, sulfated fatty acid amides, glycerol mannitan laurate, polyalkylether condensates of fatty acids, lignin sulfonates, and the like. The preferred class of surfactants for preparing compositions of this invention are blends of sulfonated oils and polyalcohol carboxylic acid esters such as the commercially available Emcol H-77, blends of polyoxyethylene ethers and oil-soluble sulfonates such as commercially available Emcol H-400, blends of alkyl aryl sulfonates and alkylphenoxy polyethoxy ethanols such as the commercially available Tritons X-151, X-161, and X-171, e.g., about equal parts of sodium dodecylbenzenesulfonate and isooctylphenoxy polyethoxy ethanol containing about 12 ethoxy groups, and blends of calcium alkyl-aryl sulfonates and polyethoxylated vegetable oils such as commercially available Agrimul N₄S. The sulfate and sulfonate surfactants discussed above are preferably used in the form of their soluble salts, for example, their sodium salts.

If desired, dispersants such as methyl cellulose, polyvinyl alcohol, sodium ligninsulfonates, and the like may be included in the dispersible powder compositions of this invention. Adhesive or sticking agents such as vegetable oils, naturally occurring gums, casein, and others may also be included. Corrosion inhibitors such as epichlorohydrin and anti-foaming agents such as stearic acid may also be added if desired.

Granular compositions of this invention are convenient for application to soil when persistence is desired. Such compositions are readily applied by broadcast or by localized, e.g., in-the-row applications. The individual granules may be any desired size from 30 to 60 mesh up to 20 to 40 mesh, or even larger. Granulars are prepared by dissolving the active compound in a solvent such as methylene chloride, xylene, or acetone and applying the solution to a quantity of a granulated absorbent carrier. Representative granulated absorbent carriers are ground corn cobs, ground walnut shells, ground peanut hulls, and the like. When desired, the impregnated granulated absorbent carrier may be coated with a coating that will preserve the integrity of the granular until it is applied to an object or situs favorable for release of the active ingredient. Such coatings are well known in the art.

The compounds (I) of the invention may also be admixed with other known pesticides to form compositions of the invention. For example, they may be mixed with malathion, azinphosmethyl, carbaryl, methoxychlor, and like pesticidal compounds.

The compounds (I) of the invention may be applied to insects, mites, objects, or a situs in aqueous sprays without a solid carrier. Such aqueous sprays are advantageous for certain types of spray equipment and conditions of application as is well known in the art. They are also advantageous when uniform dispersions, homogeneous solutions, or other easily mixed aqueous sprays are desired.

Aqueous sprays without a solid carrier are prepared from concentrated solutions of the compounds (I) of the invention in an inert organic solvent carrier. The inert organic solvent carrier may be one that is miscible or immiscible with water. The compounds (I) that are somewhat soluble in water may be dissolved in a water miscible solvent carrier, e.g., ethanol and mixed with water to give homogeneous solutions. The compounds (I) that are less soluble in water may be dissolved in a solvent carrier that is immiscible with water and the solution dispersed in water to give a uniform dispersion, e.g., an emulsion.

In an oil-in-water emulsion, the solvent phase is dispersed in the water phase and the dispersed phase contains the compound (I). In this way, uniform distribution of a water insoluble compound (I) is achieved in an aqueous spray. A solvent carrier in which the compounds (I) are highly soluble is desirable so that relatively high concentrations of the compound (I) can be obtained. One or more solvent carriers with or without a co-solvent may be used in order to obtain concentrated solutions of the compounds (I), the main consideration being to employ a water-immiscible solvent for the compound (I) that will hold the compound in solution over the range of concentration useful for applying to invertebrate pests or a situs.

The emulsifiable concentrate compositions of the invention are preferred compositions prepared by dissolving the compound (I) as the active ingredient and a surfactant such as one of those previously described, in a substantially water-immiscible solvent carreri (i.e., a solvent carrier which is soluble in water to the extent of less than 2.5% by volume at temperatures of the order of 20°C. to 30°C.), for example, cyclohexanone, methyl propyl ketone, summer oils (a paraffinic, intermediate distillation fraction having a viscosity range from 40 to 85 seconds Saybolt and an unsulfonatable residue over 90 percent), ethylene dichloride; aromatic hydrocarbons such as benzene, toluene, and xylene, and high-boiling petroleum hydrocarbons such as kerosene, diesel oil, and the like. When desired, a co-solvent such as methyl ethyl ketone, acetone, isopropanol, and the like may be included with the solvent carrier in order to enhance the solubility of the compound (I). Aqueous emulsions are prepared by mixing the concentrate with water to give any desired concentration of compounds (I).

Advantageously, the concentration of compound (I) in emulsifiable concentrates will range from about 5 percent to about 50 percent by weight, preferably from about 10 percent to about 40 percent. A concentrate comprising 20 percent by weight of the compound (I) dissolved in a water-immiscible solvent of the kind noted above may be admixed with an aqueous medium in the proportions of 13 ml. of concentrate with 1 gal. of medium to give a mixture containing 700 parts of compounds (I) per million parts of liquid carrier. Similarly, 1 qt. of a 20 percent concentrate mixed with 40 gals. of water provides about 1200 ppm (parts per million) of a compound (I). In the same manner, more concentrated solutions of active ingredient may be prepared by adjusting upward the proportion of compound (I).

The above described concentrate compositions of the invention which are intended for use in the form of aqueous dispersions or emulsions may also contain advantageously a humectant, i.e., an agent which will delay the drying of the composition in contact with material to which it has been applied. Conventionally used humectants are exemplified by glycerol, diethylene glycol, solubilized lignins, such as calicum ligninsulfonate, and the like.

For use in an aerosol, the compound (I) may be dissolved in acetone or a mixture of acetone and a heavy petroleum oil and mixed in a thick-walled canister or bomb with a propellent such as methyl chloride or dichlorodifluoromethane.

The compositions containing compounds (I) of the invention may be applied to invertebrate pests or pestiferous sites by conventional methods. For example, an area of soil, a building, or plants may be treated by spraying wettable powder suspensions, emulsions, or solutions from powder sprayers or from hand-operated knapsack sprayers. Dusts can be applied by power dusters, or by hand-operated dusters. Creams and ointment formulations may be applied to objects for prolonged protection from insects and mites.

It will of course be appreciated by those skilled in the art that the conditions encountered when applying the method and compositions of this invention to actual practice can vary widely. Among the variables that may be encountered are the degree of infestation by pests, the particular pest to be controlled, the specific compound (I) employed, the particular situs being treated, the age or degree of development of plants to be protected, the prevailing weather conditions, such as temperature, relative humidity, rainfall, dews, and like environmental conditions. Dependent upon the variables encountered in a given situation, the amount of compounds (I) to be employed as an effective amount, the frequency of application and the technique of application will be adjusted for optimum effect, as those skilled in the art well appreciate.

In general, efficacy of the compounds (I) against invertebrate pests has been demonstrated at concentrations of 1000, 500, 100, 50 and even 30 ppm of the novel compounds (I) depending upon the specific pest to be killed. Some invertebrate animal pests will be more sensitive to the compounds (I) than others. Methods of testing a given compound (I) to determine the maximum effective concentration required for killing a specific invertebrate pest are well known; see for example U.S. Pat. Nos. 3,474,170; 3,476,836; and 3,479,029. In general, effective amounts of the compounds (I) for pesticidal activity is obtained when the compounds (I) are applied at concentrations of about 30 to about 6000 ppm, preferably at concentrations of about 100 to about 4000 ppm.

The following example illustrates compositions of the invention (percentages hereafter are w/w unless otherwise specified):

EXAMPLE 23

An emulsifiable concentrate having the following percentage composition:

| | |
|---|---|
| N,N''-dithiobis[N'-(2-methyl-4-chlorophenyl)-N-methyl]-formamidine | 15.0% |
| Technical alkyl naphthalene boiling at 238° to 293° C. (Velsicol AR50) | 19.7% |
| Xylene | 17.4% |
| Acetone | 17.4% |
| Ethylene dichloride | 25.4% |
| Blend of alkyl aryl sulfonates and alkylphenoxy polyethoxy ethanols (Triton X-151) | 5.1% | was prepared by mixing 15.0 lbs. of N,N''-dithiobis[N'-(2-methyl-4-chlorophenyl)-N-methyl]formamidine, 19.7 lbs. of Velsicol AR50, 17.4 lbs. of xylene, 17.4 lbs. of acetone, 25.4 lbs. of ethylene dichloride, and 5.1 lbs. of Triton X-151.

6.67 Lbs. of the concentrate mixed with 10 gals. of water gave a spray emulsion containing about 11,000 ppm of active ingredient.

The composition is useful in treating apples for control of the two-spotted spider mite when applied at a rate of 10 gals. per acre.

EXAMPLE 24

An emulsifiable concentrate having the following percentage composition:

| | |
|---|---|
| N,N''-dithiobis[N'-(2-methyl-4-chlorophenyl)-N-methyl]-formamidine | 40.0% |
| Technical alkyl naphthalene boiling at 238° to 293° C. (Velsicol AR50) | 13.7% |
| Xylene | 12.3% |
| Acetone | 11.3% |
| Ethylene dichloride | 17.7% |
| Blend of alkyl aryl sulfonates and alkylphenoxy polyethoxy ethanol (Triton X-151) | 5.0% | was prepared by mixing 40.0 lbs. of N,N''-dithiobis[N'-(2-methyl-4-chlorophenyl)-N-methyl]formamidine, 13.7 lbs. of Velsicol AR50, 12.3 lbs. of xylene, 11.3 lbs. of acetone, 17.7 lbs. of ethylene dichloride, and 5.0 lbs. of Triton X-151.

1.67 Lbs. of the concentrate mixed with 10 gals. of water gave a spray emulsion containing about 8,000 ppm of active ingredient.

The composition is useful in treating cotton for control of the cotton bollworm when applied at a rate of 20 gals. per acre.

EXAMPLE 25

Following the procedure of the preceding Examples 23 and 24 compositions are similarly prepared substituting each of the compounds prepared in Examples 2 through 22, inclusive, for the N,N''-dithiobis([N'-(2-methyl-4-chlorophenyl)-N-methyl]formamidine.

We claim:

1. A compound of the formula:

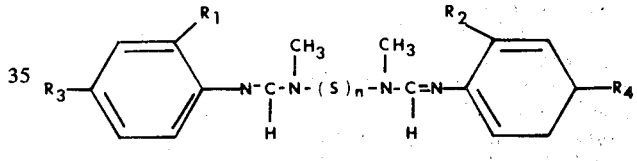

wherein $R_1$ and $R_2$ are the same or different and are selected from the group consisting of lower alkyl of from 1 to 4 carbon atoms; $R_3$ and $R_4$ are the same or different and are selected from the group consisting of hydrogen, halogen, and lower alkyl of from 1 to 4 carbon atoms, and $n$ is 1 or 2 provided that when $n$ is 2 then $R_1$ and $R_2$ are the same and $R_3$ and $R_4$ are the same.

2. A compound according to claim 1 which is N,N''-dithiobis-[N'-2,4-xylyl-N-methylformamidine].

3. A compound according to claim 1 which is N,N''-dithiobis-[N'-(2-methyl-4-chlorophenyl)-N-methylformamidine].

4. A compound according to claim 1 which is N,N''-dithiobis-[N'-(2-methyl-4-bromophenyl)-N-methylformamidine].

5. A compound according to claim 1 which is N,N''-thiobis-[N'-(2-methyl-4-bromophenyl)-N-methylformamidine].

6. A compound according to claim 1 which is N,N''-thiobis-[N'-(2-methyl-4-chlorophenyl)-N-methylformamidine].

7. A compound according to claim 1 which is N,N''-thiobis-[N'-(2,4-xylyl)-N-methylformamidine].

8. A compound according to claim 1 which is N'-(2-methyl-4-chlorophenyl)-N''''-2,4-xylyl-N,N''-thiobis[N-methylform-amidine].

9. An agricultural composition for controlling insect pest populations comprising an effective amount of a compound of the formula:

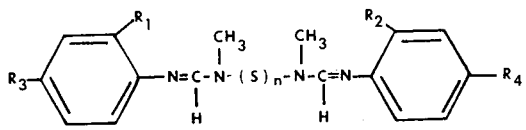

wherein $R_1$ and $R_2$ are the same or different and are selected from the group consisting of lower alkyl of from 1 to 4 carbon atoms; $R_3$ and $R_4$ are the same or different and are selected from the group consisting of hydrogen, halogen, and lower alkyl of from 1 to 4 carbon atoms, and $n$ is 1 or 2 provided that when $n$ is 2 then $R_1$ and $R_2$ are the same and $R_3$ and $R_4$ are the same; in association with an agricultural carrier.

10. A composition according to claim 9 wherein the said compound is present in a concentration of from about 0.001 w/w to about 80% w/w.

11. A composition according to claim 10 wherein the said compound is N,N''-thiobis[N'-(2-methyl-4-chlorophenyl)-N-methylformamidine].

12. A composition according to claim 10 wherein the said compound is N,N''-dithiobis[N'-2,4-xylyl-N-methylformamidine].

13. A composition according to claim 10 wherein the said compound is N,N''-dithiobis[N'-(2-methyl-4-chlorophenyl)-N-methylformamidine].

14. A composition according to claim 10 wherein the said compound is N,N''-dithiobis[N'-(2-methyl-4-bromophenyl)-N-methylformamidine].

15. A composition according to claim 10 wherein the said compound is N,N''-thiobis[N'-(2-methyl-4-bromophenyl)-N-methylformamidine].

16. A composition according to claim 10 wherein the said compound is N,N''-thiobis[N'-(2,4-xylyl)-N-methylformamidine].

17. A composition according to claim 10 wherein the said compound is N'-(2-methyl-4-chlorophenyl)-N''''-2,4-xylyl-N,N''-thiobis[N-methylformamidine].

18. A process for controlling insect pest populations which comprise applying to a situs effective amounts of a compound of the formula:

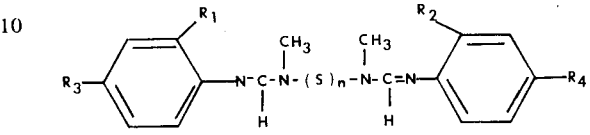

wherein $R_1$ and $R_2$ are the same or different and are selected from the group consisting of lower alkyl of from 1 to 4 carbon atoms; $R_3$ and $R_4$ are the same or different and are selected from the group consisting of hydrogen, halogen, and lower alkyl of from 1 to 4 carbon atoms, and $n$ is 1 or 2 provided that when $n$ is 2 then $R_1$ and $R_2$ are the same and $R_3$ and $R_4$ are the same.

19. The process of claim 18 wherein the compound is N,N''-thiobis[N'-(2-methyl-4-chlorophenyl)-N-methylformamidine].

20. The process of claim 18 wherein the compound is N,N''-dithiobis[N'-2,4-xylyl-N-methylformamidine].

21. The process of claim 18 wherein the compound is N,N''-dithiobis[N'-(2-methyl-4-chlorophenyl)-N-methylformamidine].

22. The process of claim 18 wherein the compound is N,N''-dithiobis[N'-(2-methyl-4-bromophenyl)-N-methylformamidine].

23. The process of claim 18 wherein the compound is (N, N''-thiobis[N'-(2-methyl-4-bromophenyl)-N-methyl-formamidine].

24. The process of claim 18 wherein the compound is N,N''-thiobis[N'-(2,4-xylyl)-N-methylformamidine].

25. The process of claim 18 wherein the compound is N''-(2-methyl-4-chlorophenyl) -N'''-2,4-xylyl-N,N''-thiobis-[N-methylformamidine].

* * * * *